United States Patent [19]

Ando et al.

[11] Patent Number: 4,742,298
[45] Date of Patent: May 3, 1988

[54] APPARATUS FOR DETECTING SURFACE FLAW OF PIPELINE BY ELECTROMAGNETIC INDUCTION

[75] Inventors: Seigo Ando, Yokohama; Toshiaki Hosoe, Yokosuka, both of Japan

[73] Assignee: Nippon Kokan Kabushiki Kaisha, Tokyo, Japan

[21] Appl. No.: 907,840

[22] Filed: Sep. 16, 1986

[51] Int. Cl.⁴ .................. G01N 27/82; G01R 33/12
[52] U.S. Cl. .................. 324/220; 324/225; 324/242
[58] Field of Search .................. 324/219–221, 324/239–243, 225, 233

[56] References Cited

U.S. PATENT DOCUMENTS

| | | | |
|---|---|---|---|
| 2,124,579 | 7/1938 | Knerr et al. | 324/242 X |
| 2,555,853 | 6/1951 | Irwin | 324/242 |
| 3,593,122 | 7/1971 | Barton | 324/220 |
| 3,597,678 | 8/1971 | Fearon | 324/220 |
| 4,105,972 | 8/1978 | Smith . | |
| 4,649,343 | 3/1987 | Birchak et al. | 324/242 X |

FOREIGN PATENT DOCUMENTS

| | | |
|---|---|---|
| 00119091A1 | 11/1980 | European Pat. Off. . |
| 0065325A3 | 11/1982 | European Pat. Off. . |
| 2018637 | 6/1970 | France . |
| 0101044 | 8/1980 | Japan | 324/220 |
| 60-11157 | 1/1985 | Japan . |
| 1586581 | 3/1981 | United Kingdom . |

*Primary Examiner*—Gerard R. Strecker
*Attorney, Agent, or Firm*—Frishauf, Holtz, Goodman & Woodward

[57] ABSTRACT

An apparatus for detecting a surface flaw of each pipe constituting a pipeline, including a pig capable of travelling along pipeline and being provided with the following elements: a cylindrical primary coil coaxial with the pipe, the density of a magnetic flux of an AC magnetic field of the primary coil varying in response to an inner surface flaw of the pipe; a plurality of cylindrical secondary coils arranged at prescribed intervals in the circumferential direction of the pipe between a peripheral surface of the primary coil and a confronting peripheral surface of the pipe, each secondary coil having an axis parallel to the axis of the primary coil, and producing an AC voltage proportional to the density of a component parallel to the axis of each secondary coil, of the magnetic flux of the AC magnetic field of the primary coil; and a signal processing circuit for processing the AC voltage signals from the secondary coils to detect the presence and the depth of a surface flaw of the pipe.

5 Claims, 4 Drawing Sheets

APPARATUS FOR DETECTING SURFACE FLAW OF PIPELINE BY ELECTROMAGNETIC INDUCTION

PATENTS, APPLICATIONS AND PUBLICATIONS PERTINENT TO THE INVENTION

As far as we know, there is available the following prior art document pertinent to the present invention: Japanese Patent Provisional Publication No. 60-11,157 dated Jan. 21, 1985.

The contents of the above-mentioned prior art document will be discussed hereafter under the heading of the "BACKGROUND OF THE INVENTION".

FIELD OF THE INVENTION

The present invention relates to an apparatus for detecting an inner surface flaw of each pipe constituting a pipeline.

BACKGROUND OF THE INVENTION

An apparatus for detecting a surface flaw of a pipe with the use of electromagnetic induction is publicly known. For example, an apparatus for detecting an outer surface flaw of a pipe with the use of electromagnetic induction is disclosed in Japanese Patent Provisional Publication No. 60-11,157 dated Jan. 21, 1985, which comprises: at least one cylindrical primary coil, a high frequency electric current generator, a plurality of probe coils, i.e., a plurality of cylindrical secondary coils, a multiplexer and a signal processing circuit (hereinafter referred to as the "prior art").

The at least one primary coil surrounds a pipe to be inspected, and is coaxial with the pipe. In other words, the pipe is coaxially inserted into the at least one primary coil. The inner peripheral surface of the at least one primary coil is spaced apart from the outer peripheral surface of the pipe by a prescribed distance.

The high frequency electric current generator supplies high frequency electric current to the at least one primary coil to cause the at least one primary coil to produce an AC magnetic field, and the magnetic flux density of the AC magnetic field varies in response to an outer surface flaw of the pipe.

The plurality of secondary coils are arranged along the outer surface of the pipe at prescribed intervals in the circumferential direction of the pipe in the close vicinity of the at least one primary coil. The axis of each of the plurality of secondary coils is arranged at right angles to the axis of the at least one primary coil. Each of the plurality of secondary coils produces an AC voltage proportional to the density of a component parallel to the axial direction of each of the plurality of secondary coils, of the magnetic flux interlinking with each of the plurality of secondary coils, of the AC magnetic field of the at least one primary coil. The plurality of secondary coils constitute, together with the at least one primary coil, a detecting probe, and the detecting probe is moved relative to the pipe in the axial direction of the coil.

The multiplexer repeatedly takes out the AC voltage signals from the plurality of secondary coils sequentially in the order of arrangement of the plurality of secondary coils at a prescribed sampling cycle period T.

The signal processing circuit comprises a synchronous detector, a delay circuit and an adder.

The synchronous detector sequentially and synchronously detects the AC voltage signals from the plurality of secondary coils, taken out by the multiplexer, with the high frequency electric current from the high frequency electric current generator as the reference signal, thereby eliminating noise signals from the AC voltage signals from the plurality of secondary coils, and at the same time, converting the AC voltage signals into DC voltage signals. Each value of the thus converted DC voltage signals is proportional to the depth of an outer surface flaw of the pipe.

The delay circuit causes delay of the DC voltage signals from the synchronous detector by a period of time equal to the above-mentioned sampling cycle period T.

The adder adds the thus delayed DC voltage signal from the delay circuit to a DC voltage signal from the synchronous detector in the next sampling cycle period for each of the plurality of secondary coils, thereby obtaining a DC voltage signal with a minimized detection error in the pipe axial direction of the outer surface flaw of the pipe for each of the plurality of secondary coils.

In the above-mentioned prior art, it is possible to detect the presence and the depth of the outer surface flaw of the pipe with a minimized detection error in the axial direction of the pipe, by sequentially detecting a differential voltage signal proportional to the depth of the outer surface flaw of the pipe, which is obtained by subtracting the bias voltage signal of each of the secondary coils resulting from an inclination or other condition of each of the secondary coils, on the one hand, from the DC voltage signal from the adder for each of the secondary coils, on the other hand.

According to the prior art, it is possible to detect an outer surface flaw of the pipe without overlooking any other surface flaw in the pipe axial direction, even when carrying out detecting operation of the outer surface flaw of the pipe while moving, relative to the pipe, the detecting probe comprising the at least one primary coil and the plurality of secondary coils at a high speed in the axial direction of the pipe.

The above-mentioned prior art, which relates to the detection of an outer surface flaw of a pipe, is also applicable to the detection of an inner surface flaw of each pipe constituting a pipeline, by causing the detecting probe comprising the at least one primary coil and the plurality of secondary coils to travel through the pipeline. However, when detecting any of the outer surface flaw or the inner surface flaw of the pipe, the prior art has the following drawbacks.

More specifically, the magnetic flux of the AC magnetic field of the at least one primary coil, which is distributed in the axial direction of the pipe in the space near the outer surface or the inner surface of the pipe, comes into an outer or inner surface flaw of the pipe, if any, and as a result, the magnetic flux density in the space near the pipe portion containing the outer or inner surface flaw shows a normal distribution having a peak of the lowest density at the position of the flaw center. This means that, the magnetic flux has the lowest density at the position of the flaw center, and consists only of a component parallel to the axial direction of the at least one primary coil. On the other hand, the magnetic flux has the highest density at the position distant from the flaw center, and consists only of a component parallel to the axial direction of the at least one primary coil. In the middle between the position of the flaw center and the position distant from the flaw center, the magnetic flux density becomes higher as the distance from the position of the flaw center increases. The magnetic flux is analyzed into a component parallel to the axial direction of the at least one primary coil and a component at right angles to the axial direction of the at least one primary coil, and the latter component increases as the distance from the position of the flaw center increases to reach the maximum, and then decreases. Therefore, in a space near the pipe portion containing an outer or inner surface flaw, the highest density of the component of the magnetic flux, which component is at right angles to the axial direction of the at least one primary coil, exists in the middle between the position of the flaw center and the position distant from the flaw center.

The difference in the magnetic flux density between the lowest density at the position of the flaw center and the highest density at the position distant from the flaw center corresponds to the depth of the flaw. The highest density of the component of the magnetic flux, which component is at right angles to the axial direction of the at least one primary coil, at a position between the position of the flaw center and the position distant from the flaw center also corresponds to the depth of the flaw. Since, in the above-mentioned prior art, the plurality of secondary coils are arranged so that the axis of each of the plurality of secondary coils is at right angles to the axis of the at least one primary coil, each of the plurality of secondary coils senses a component at right angles to the axial direction of the at least one primary coil, i.e., a component parallel to the axial direction of each of the plurality of secondary coils, of the magnetic flux of the AC magnetic field of the at least one primary coil, which magnetic flux interlinks with each of the plurality of secondary coils, and produces an AC voltage proportional to the density of the above-mentioned component. Therefore, it is possible to detect the depth of the outer surface flaw or the inner surface flaw of the pipe, by processing the AC voltage signal produced by each of the plurality of secondary coils.

However, when a first flaw, a second flaw and a third flaw each having a respective depth are present in this order on the outer or inner surface of the pipe at close intervals in the axial direction of the pipe, the density of the magnetic flux in the axial direction of the pipe, of the AC magnetic field of the at least one primary coil, in the space near the pipe portion containing these flaws, shows a distribution in which three normal distributions of the magnetic flux density corresponding respectively to these three flaws partly overlap in the axial direction of the pipe. In such a distribution of the magnetic flux density, a distribution of the magnetic flux density at a position between the center position of the first flaw and a position opposite to the second flaw relative to the first flaw, and a distribution of the magnetic flux density at a position between the center position of the third flaw and a position opposite to the second flaw relative to the third flaw, are not affected by the distribution of the magnetic flux density corresponding to the second flaw. Therefore, the highest densities of the components at right angles to the axial direction of the at least one primary coil of the magnetic flux in these two intermediate positions correspond respectively to the depth of the first flaw and the depth of the third flaw. On the contrary, a distribution of the magnetic flux density at a position between the center position of the first flaw and the center position of the second flaw, and a distribution of the magnetic flux density at a position between the center position of the second flaw and the center position of the third flaw, are affected by the distributions of the magnetic flux density corresponding respectively to the first flaw and the third flaw. Therefore, the highest densities of the components at right angles to the axial direction of the at least one primary coil of the magnetic flux in these two intermediate positions do not accurately correspond to the depth of the second flaw. Thus, the depth of the second flaw cannot be accurately detected by the prior art.

Also when four or more flaws are present on the outer or inner surface of the pipe at close intervals in the axial direction of the pipe, the same problem as described above is posed for the flaws other than those at the both ends.

Under such circumstances, there is a strong demand for the development of an apparatus for detecting, with the use of electromagnetic induction, an inner surface flaw of each pipe constituting a pipeline, which, when detecting an inner surface flaw of each of a plurality of pipes forming the pipeline, permits accurate detection of the depth of each of three or more inner surface flaws of the pipe even when these inner surface flaws exist on the inner surface of the pipe at close intervals in the axial direction of the pipe, but an apparatus provided with such properties has not as yet been proposed.

SUMMARY OF THE INVENTION

An object of the present invention is therefore to provide an apparatus for detecting, with the use of electromagnetic induction, an inner surface flaw of each of a plurality of pipes forming a pipeline, which, permits accurate detection of the depth of each of three or more inner surface flaws of the pipe even when these inner surface flaws exist on the inner surface of the pipe at close intervals.

According to the invention, in apparatus for detecting a surface a surface flaw of a pipeline using electromagnetic induction, the apparatus being of the kind including at least one primary coil arranged to interact electromagnetically with the pipeline, a generator for supplying high frequency electric current to the primary coil to produce an AC magnetic field wherein a flux density of the AC field varies in response to a surface flaw of the pipeline, a number of secondary coils arranged at intervals in the circumferential direction of the pipeline in a clearance space between confronting surfaces of the primary coil and the pipeline wherein each of the secondary coils produces an AC voltage signal proportional to a flux density of an interlinking magnetic flux component of the AC magnetic field produced by the primary coil, a multiplexer to which the secondary coils are coupled and which responds to the AC voltage signals from the secondary coils, and a signal processing circuit including a synchronous detector, moving average circuit means and flaw detecting circuit means, the improvement comprising:

said signal processing circuit includes a detection error correcting circuit for amplifying a voltage signal from the flaw detecting circuit means for each of the secondary coils, wherein the detection error correcting circuit includes means for setting an amplification factor of the detection error correcting circuit at a value inversely proportional to a value of processed DC voltage signals from the moving average circuit means for each of the secondary coils, wherein an error in the voltage signal produced by the flaw detecting circuit means, caused by a fluctuation in distance between each of the secondary coils and the peripheral surface of the pipeline which confronts the primary coil, is corrected.

DETAILED DESCRIPTION OF PREFERRED EMBODIMENTS

From the above-mentioned point of view, extensive studies were carried out to develop an apparatus for detecting, with the use of electromagnetic induction, an inner surface flaw of each of a plurality of pipes forming a pipeline, which permits accurate detection of the depth of each of three or more inner surface flaws of the pipe even when these inner surface flaws exist on the inner surface of the pipe at close intervals in the axial direction of the pipe.

As a result, the following findings were obtained: When a first flaw, a second flaw and a third flaw each having a respective depth are present in this order on the inner surface of the pipe at close intervals in the axial direction of the pipe, the density of the magnetic flux in the axial direction of the pipe, of the AC magnetic field of the at least one primary coil, in the space near the pipe portion containing these inner surface flaws, shows a distribution in which three normal distributions of the magnetic flux density corresponding respectively to these three inner surface flaws partly overlap in the axial direction of the pipe. Even in such a distribution of the magnetic flux density, the magnetic flux densities at the center positions of the first, the second and the third inner surface flaws correspond respectively to these respective flaws. Therefore, the magnetic flux densities at the center positions of the first, the second and the third inner surface flaws present the lowest values corresponding to the respective flaws, and each magnetic flux consists only of a component parallel to the axial direction of the at least one primary coil. The difference in the magnetic flux density between the lowest density of the magnetic flux at the center position of each of the first, the second and the third inner surface flaws, on the one hand, and the highest density of the magnetic flux at a position distant from each of these flaws, on the other hand, corresponds to the depth of each of the first, the second and the third inner surface flaws. Therefore, by arranging a plurality of secondary coils so that the axis of each of the plurality of secondary coils is parallel to the axis of the at least one primary coil, each of the plurality of secondary coils senses a component parallel to the axial direction of each of the plurality of secondary coils, of the magnetic flux of the AC magnetic field of the at least one primary coil, which magnetic flux interlinks with each of the plurality of secondary coils, and produces an AC voltage proportional to the density of the above-mentioned component. Thus, it is possible to accurately detect the depth of each of the first, the second and the third inner surface flaws of the pipe, by processing the AC voltage signal produced by each of the plurality of secondary coils.

The present invention was made on the basis of the above-mentioned findings. Now, an embodiment of the apparatus of the present invention for detecting an inner surface flaw of each of a plurality of pipes forming a pipeline is described with reference to the drawings.

Figure 1:
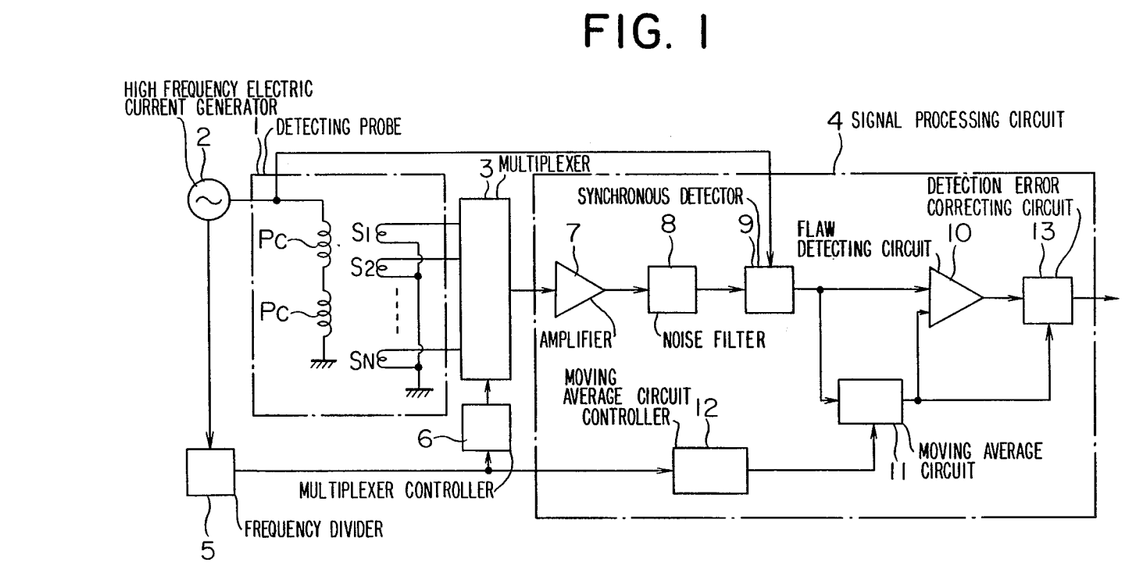
FIG. 1 is a block diagram illustrating the basic structure of an embodiment of the apparatus of the present invention for detecting an inner surface flaw of each of a plurality of pipes forming a pipeline.

FIG. 1 is a block diagram illustrating the basic structure of an embodiment of the apparatus of the present invention for detecting an inner surface flaw of each of a plurality of pipes forming a pipeline. As shown in FIG. 1, the apparatus of the present invention basically comprises a pig not shown, a pair of cylindrical primary coils $P_c$, which may be only one primary coil, mounted on the pig, a high frequency electric current generator 2 mounted on the pig, a plurality of cylindrical secondary coils $S_1, \ldots, S_N$ mounted on the pig, a multiplexer 3 mounted on the pig, and a signal processing circuit 4 mounted on the pig. The pair of primary coils $P_c$ and the plurality of secondary coils $S_1, \ldots, S_N$ form a detecting probe 1.

The pig is capable of travelling through a pipeline in the axial direction of each of a plurality of pipes forming the pipeline.

Figure 2:
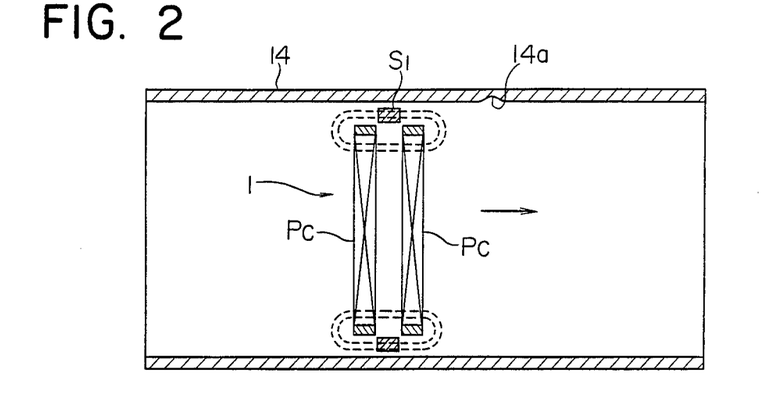
FIG. 2 is a longitudinal sectional view illustrating the positional relationship between the detecting probe which is one of the components of the apparatus of the present invention shown in FIG. 1 and a pipe to be inspected.

The pair of primary coils $P_c$ forming part of the detecting probe 1 are arranged at a prescribed interval in the axial direction of the pipe 14 as shown in FIG. 2. The pair of primary coils $P_c$ are coaxial with the pipe 14, and the outer peripheral surfaces of the pair of primary coils $P_c$ are spaced apart from the inner peripheral surface of the pipe 14 by a prescribed distance. The primary coils $P_c$ are arranged in a pair at a prescribed interval in the axial direction of the pipe 14 for the purpose of causing the magnetic flux of the AC magnetic field produced by the pair of primary coils $P_c$ to be distributed in the axial direction of the pipe 14 in the space between the outer peripheral surfaces of the pair of primary coils $P_c$ and the inner peripheral surface of the pipe 14. This allows the magnetic flux to effectively interlink with the plurality of secondary coils $S_1, \ldots, S_N$, each of which senses a component parallel to the axial direction of each of the plurality of secondary coils $S_1, \ldots, S_N$, of the magnetic flux of the AC magnetic field of the pair of primary coils $P_c$, and produces an AC voltage proportional to the density of the above-mentioned component. Therefore, by increasing the coil width of the primary coil $P_c$, it suffices to provide only one primary coil $P_c$.

The high frequency electric current generator 2 supplies high frequency electric current to the pair of primary coils $P_c$ to cause the pair of primary coils $P_c$ to produce an AC magnetic field. The magnetic flux density of the AC magnetic field of the pair of primary coils $P_c$ varies in response to an inner surface flaw 14a of the pipe 14. With a view to increasing the detection sensitivity of the inner surface flaw of the pipe 14 by the plurality of secondary coils $S_1, \ldots, S_N$, it is desirable to concentrate the magnetic flux of the AC magnetic field of the pair of primary coils $P_c$ into the space between the outer peripheral surfaces of the pair of primary coils $P_c$ and the inner peripheral surface of the pipe 14 so that the magnetic flux penetrates only into the inner surface portion of the pipe 14, thereby increasing the density of the magnetic flux in that space. In general, the penetration depth $\delta$ of the magnetic flux of the magnetic field of the primary coil into the material is determined from the frequency f of high frequency electric current supplied to the primary coil, electric conductivity $\sigma$ of the material and the magnetic permeability $\mu$ of the material, and is expressed by the formula: $\delta = 1/\sqrt{f\sigma\mu}$. It suffices therefore to cause the high frequency electric current generator 2 to generate a high frequency electric current having a proper frequency in response to the material of the pipe 14 so that the magnetic flux of the AC magnetic field of the pair of primary coils $P_c$ penetrates only into the inner surface portion of the pipe 14.

Figure 3:
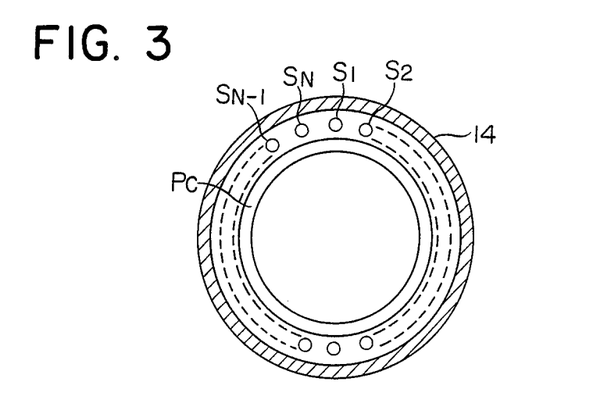
FIG. 3 is a transverse sectional view illustrating the arrangement of the pair of primary coils and the plurality of secondary coils, which constitute the detecting probe shown if FIG. 2.

As shown in FIG. 3, the plurality of secondary coils $S_1, \ldots, S_N$ are arranged at prescribed intervals in the circumferential direction of the pipe 14 in the space between the outer peripheral surfaces of the pair of primary coils $P_c$ and the inner peripheral surface of the pipe 14. The axis of each of the plurality of secondary coils $S_1, \ldots, S_N$ is parallel to the axis of each of the pair of primary coils $P_c$ so as to permit an accurate detection by the plurality of the secondary coils $S_1, \ldots, S_N$, even when three or more inner surface flaws 14a each having a respective depth are present on the inner surface of the pipe 14 at close intervals in the axial direction of the pipe 14, of the depth of each of these inner surface flaws 14a. Even when three or more inner surface flaws 14a each having a respective depth are present on the inner surface of the pipe 14 at close intervals in the axial direction of the pipe 14, the lowest density of the magnetic flux of the AC magnetic field of the pair of primary coils $P_c$ at the center position of each of these inner surface flaws 14a in the space near the portion of the pipe 14 containing these inner surface flaws 14a corresponds only to each of these inner surface flaws 14a, and the magnetic flux consists only of a component parallel to the axial direction of the pair of primary coils $P_c$. The difference in the magnetic flux density between the lowest density of the magnetic flux at the center position of each of these inner surface flaws 14a, on the one hand, and the highest density of the magnetic flux at a position distant from each of these inner surface flaws 14a, on the other hand, corresponds to the depth of each of these inner surface flaws 14a. Therefore, by arranging the plurality of secondary coils $S_1, \ldots, S_N$ as described above, each of the plurality of secondary coils $S_1, \ldots, S_N$ senses a component parallel to the axial direction of each of the plurality of secondary coils $S_1, \ldots, S_N$, of the magnetic flux of the AC magnetic field of the pair of primary coils $P_c$, which magnetic flux interlinks with each of the plurality of secondary coils $S_1, \ldots, S_N$, and produces an AC voltage proportional to the density of the above-mentioned component, thus, permitting an accurate detection of the presece and the depth of each of these inner surface flaws 14a.

When there is no inner surface flaw 14a on the inner surface of the pipe 14, there is no change in the density of the component parallel to the axial direction of each of the plurality of secondary coils $S_1, \ldots, S_N$, of the magnetic flux of the AC magnetic field of the pair of primary coils $P_c$, which magnetic flux interlinks with each of the plurality of secondary coils $S_1, \ldots, S_N$. Therefore, each of the plurality of secondary coils $S_1, \ldots, S_N$ produces a constant AC voltage. On the other hand, when a distance between the outer peripheral surfaces of the pair of primary coils $P_c$ and the inner peripheral surface of the pipe 14 is changed, the density of the above-mentioned component parallel to the axial direction of each of the plurality of secondary coils $S_1, \ldots, S_N$, of the magnetic flux of the AC magnetic field of the pair of primary coils $P_c$ is changed in response to the thus changed distance. Therefore, each of the plurality of secondary coils $S_1, \ldots S_N$ produces an AC voltage corresponding to the thus changed distance.

As is clear from the foregoing, when the detecting probe 1 travels through the pipe 14 in the arrow direction in FIG. 2 along with the travel of the pig until the pair of primary coils $P_c$ reach the inner surface flaw 14a of the pipe 14, a secondary coil $S_1$ closest to the inner surface flaw 14a, for example, among the plurality of secondary coils $S_1, \ldots, S_N$ produces an AC voltage corresponding not only to the depth of the inner surface flaw 14a, but also to the distance between the outer peripheral surfaces of the pair of primary coils $P_c$ and the inner peripheral surface of the pipe 14, i.e., between the secondary coil $S_1$ and the inner peripheral surface of the pipe 14.

Figure 4:
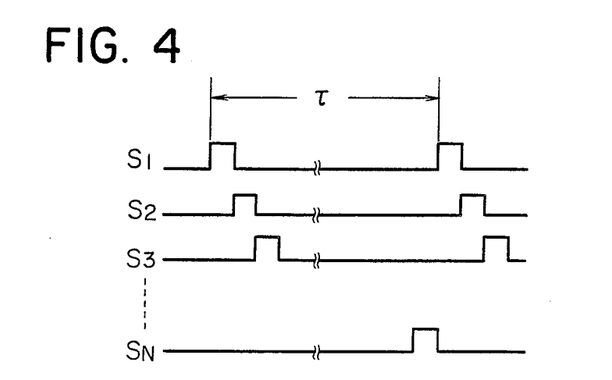
FIG. 4 is a timing chart illustrating the timing for taking out an AC voltage from the plurality of secondary coils by the multiplexer which is one of the components of the apparatus of the present invention shown in FIG. 1.

The multiplexer 3 repeatedly takes out the AC voltage signals from the plurality of secondary coils $S_1, \ldots, S_N$ sequentially in the order of arrangement thereof at a prescribed sampling cycle period $\tau$ as shown in FIG. 4. Operations of the multiplexer 3 are controlled by control signals from a multiplexer controller 6. The control signal is created, as shown in FIG. 1, in the multiplexer controller 6 on the basis of the high frequency electric current from the high frequency electric current generator 2, which has been divided by a frequency divider 5 into a frequency having a prescribed value.

The sampling cycle period $\tau$ of the AC voltage signals from the plurality of secondary coils $S_1, \ldots, S_N$ is set in accordance with conditions for the detection of the inner surface flaw 14a, and usually ranges from 1/10⁴ to 1/10 seconds.

The signal processing circuit 4 basically comprises, as shown in FIG. 1, a synchronous detector 9, a moving average circuit 11, a flaw detecting circuit 10 and a detection error correcting circuit 13, and has, in addition, an amplifier 7, a noise filter 8 and a moving average circuit controller 12.

The AC voltage signals from the plurality of secondary coils $S_1, \ldots, S_N$, taken out by the multiplexer 3 are amplified by the amplifier 7, then entered into the synchronous detector 9 after the preliminary elimination of noise signals by the noise filter 8.

The synchronous detector 9 sequentially and synchronously detects the AC voltage signals from the plurality of secondary coils $S_1, \ldots, S_N$, which have passed through the amplifier 7 and the noise filter 8, with the high frequency electric current from the high frequency electric current generator 2 as the reference signal, thereby eliminating noise signals from the AC voltage signals from the plurality of secondary coils $S_1, \ldots, S_N$, and at the same time, converting the AC voltage signals into DC voltage signals.

As described above, when the pair of primary coils $P_c$ do not reach the inner surface flaw 14a of the pipe 14, each of the plurality of secondary coils $S_1, \ldots, S_N$ produces an AC voltage corresponding to the distance between the outer peripheral surfaces of the pair of primary coils $P_c$ and the inner peripheral surface of the pipe 14, i.e., between each of the plurality of secondary coils $S_1, \ldots, S_N$ and the inner peripheral surface of the pipe 14. When the pair of primary coils $P_c$ reach the inner surface flaw 14a along with the travel of the detecting probe 1, the secondary coil $S_1$ closest to the inner surface flaw 14a, for example, among the plurality of secondary coils $S_1, \ldots, S_N$ produces an AC voltage corresponding not only to the depth of the inner surface flaw 14a, but also to the distance between the secondary coil $S_1$ and the inner peripheral surface of the pipe 14. Therefore, the distance between the secondary coil $S_1$ and the inner peripheral surface of the pipe 14 appears as a bias voltage signal of the DC voltage signal converted by the synchronous detector 9 from the AC voltage signal from the secondary coil $S_1$. More specifically, when the pair of primary coils $P_c$ do not reach the inner surface flaw 14a, the above-mentioned bias voltage signal for the secondary coil $S_1$ is equal to the DC voltage signal from the secondary coil $S_1$. The depth of the inner surface flaw 14a appears as a differential, which is obtained by subtracting the bias voltage signal from voltage signal between the DC voltage signal from the synchronous detector 9 corresponding to the AC voltage signal from the secondary coil $S_1$ closest to the inner surface flaw 14a.

Figure 5:
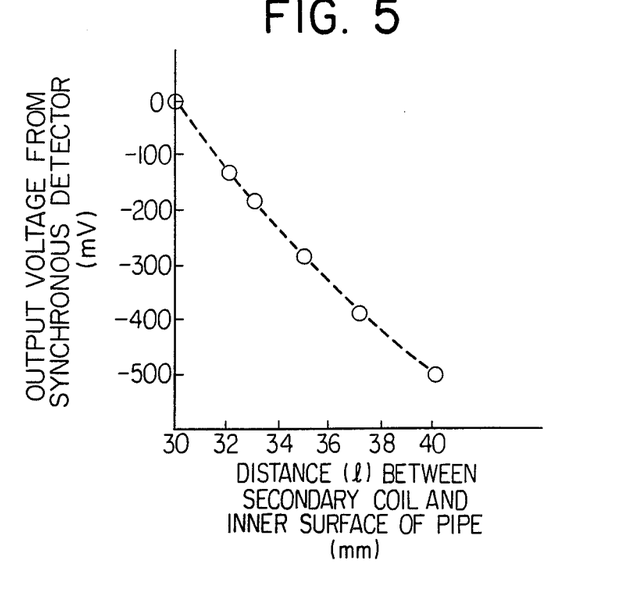
FIG. 5 is a graph illustrating the relationship between the output voltage from the synchronous detector of the signal processing circuit, which is one of the components of the apparatus of the present invention shown in FIG. 1, on the one hand, and the distance (l) between the secondary coil and the inner surface of a pipe to be inspected, on the/other hand.

FIG. 5 is a graph illustrating the relationship between the output voltage from the synchronous detector, on the one hand, and the distance (l) between the outer peripheral surfaces of the primary coils and the inner peripheral surface of the pipe, i.e., between the secondary coil and the inner peripheral surface of the pipe 14, on the other hand. In FIG. 5, the ordinate represents the value of the DC voltage signal from the synchronous detector 9, i.e., the value of the bias voltage signal, corresponding to the value of the AC voltage signal from the secondary coil $S_1$, for example, of the plurality of secondary coils $S_1, \ldots, S_N$ in the case where there is no inner surface flaw 14a on the inner surface of the pipe 14. The abscissa represents the distance (l) between that secondary coil $S_1$ and the inner peripheral surface of the pipe 14. The output voltage from the synchronous detector 9 represented on the ordinate shows values with the output voltage at a distance (l) of 30 mm as zero V. The high frequency electric current supplied to the pair of primary coils $P_c$ has a frequency of 100 kHz.

As is clear from FIG. 5, the output voltage from the synchronous detector 9 in the case where there is no inner surface flaw 14a decreases almost linearly as the distance (l) between the secondary coil $S_1$ and the inner peripheral surface of the pipe 14 increases. This demonstrates that the value of the bias voltage signal from the synchronous detector 9 varies in proportion to the distance (l).

Figure 6:
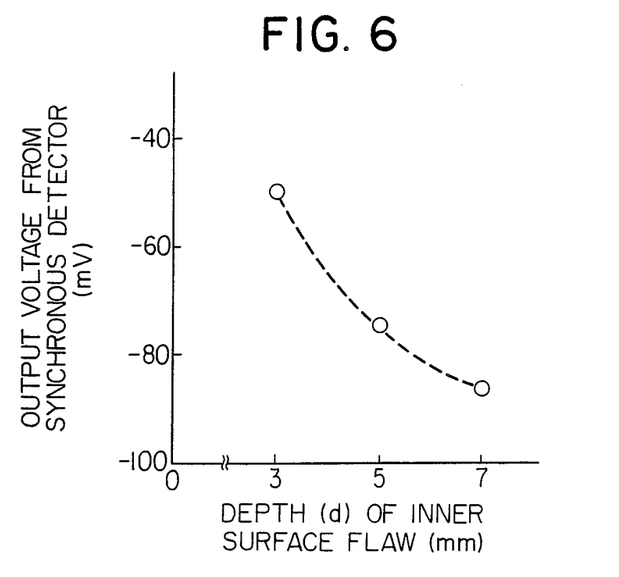
FIG. 6 is a graph illustrating the relationship between the output voltage from the synchronous detector of the signal processing circuit, which is one of the components of the apparatus of the present invention shown in FIG. 1, on the one hand, and the depth (d) of an inner surface flaw of a pipe to be inspected, on the other hand.

FIG. 6 is a graph illustrating the relationship between the output voltage from the synchronous detector and the depth (d) of an inner surface flaw of the pipe. In FIG. 6, the ordinate represents the value of the DC voltage signal from the synchronous detector 9, corresponding to the value of the AC voltage signal from the secondary coil $S_1$ closest to the inner surface flaw 14a of the pipe 14, for example, of the plurality of secondary coils $S_1, \ldots, S_N$, in the case where the pair of primary coils $P_c$ reach the inner surface flaw 14a. The abscissa represents the depth (d) of the inner surface flaw 14a. The output voltage from the synchronous detector 9 represented on the ordinate shows values with the output voltage in the case where the pair of primary coils $P_c$ do not reach the inner surface flaw 14a as zero V. The inner surface flaw 14a was artificially made by a drill. The inner surface flaw 14a has a diameter of 30 mm. The distance (l) between the secondary coil $S_1$ and the inner peripheral surface of the pipe 14 is 30 mm, and the high frequency electric current supplied to the pair of primary coils $P_c$ has a frequency of 100 kHz.

As is clear from FIG. 6, the output voltage from the synchronous detector 9 decreases as the depth (d) of the inner surface flaw 14a increases. Therefore, the depth (d) of the inner surface flaw 14a can be detected from the value of the DC voltage signal from the synchronous detector 9.

However, as is clear from FIGS. 5 and 6, the variation in the output voltage from the synchronous detector 9 corresponding to the variation in the depth (d) of the inner surface flaw 14a is smaller than the variation in the output voltage from the synchronous detector 9 corresponding to the variation in the distance (l) between the secondary coil $S_1$ and the inner surface of the pipe 14. Therefore, detection of the differential voltage signal between the DC voltage signal and the bias voltage signal by detecting the variation in voltage of the DC voltage signal from the synchronous detector 9 not only gives a low detection sensitivity of the depth (d) of the inner surface flaw 14a, but also causes the risk of taking the variation in the distance (l) for the depth (d) of the inner surface flaw 14a. Therefore, it is necessary to obtain the differential voltage signal proportional to the depth (d) of the inner surface flaw 14a, between the DC voltage signal which is entered from the synchronous detector 9 directly into the flaw detecting circuit 10, on the one hand, and the DC voltage signal which has been entered from the synchronous detector 9 into the moving average circuit 11 and has been moving-averaged there and is then entered from the moving average circuit 11 into the flaw detecting circuit 10, on the other hand.

More specifically, the moving average circuit 11 moving-averages the DC voltage signals in a prescribed number from the synchronous detector 9 for each of the plurality of secondary coils $S_1, \ldots, S_N$, thereby sequentially taking out bias voltage signals from the DC voltage signals for each of the plurality of secondary coils $S_1, \ldots, S_N$.

The number of DC voltage signals from the synchronous detector 9 to be moving-averaged is usually 3 to 10. Operation of the moving average circuit 11 is controlled by control signals from the moving average circuit controller 12. The control signal is created, as shown in FIG. 1, in the moving average circuit controller 12 on the basis of the high frequency electric current from the high frequency electric current generator 2, which has been divided by the frequency divider 5 into a frequency having a prescribed value. According to the above-mentioned takeout of the bias voltage signals by the moving average circuit 11, it is possible to obtain the bias voltage signals from which the noise signals caused, for example, by the inclination of each of the plurality of secondary coils $S_1, \ldots, S_N$ have been eliminated.

The flaw detecting circuit 10 sequentially detects a differential voltage signal proportional to the depth (d) of the inner surface flaw 14a of the pipe 14, which is obtained by subtracting the bias voltage signal from the moving average circuit 11 for each of the plurality of secondary coils $S_1, \ldots, S_N$, on the one hand, from and a DC voltage signal from the synchronous detector 9, which immediately follows the moving-averaging effected by means of the moving average circuit 11, for each of the plurality of secondary coils $S_1, \ldots, S_N$, on the other hand. By detecting the above-mentioned differential voltage signal, it is possible to detect the depth (d) of the inner surface flaw 14a at a high detection sensitivity and without confusing with the change in the distance (l) between each of the plurality of secondary coils $S_1, \ldots, S_N$ and the inner peripheral surface of the pipe 14.

However, along with the change in the distance (l) between each of the plurality of secondary coils $S_1, \ldots, S_N$ and the inner surface of the pipe 14, there occurs a change in the portion of the AC voltage from each of the secondary coils $S_1, \ldots, S_N$, corresponding to the depth (d) of the inner surface flaw 14a. More particularly, not only the bias voltage signal of the DC voltage signal from the synchronous detector 9, but also the differential voltage signal between the DC voltage signal and the bias voltage signal are affected by the change in the distance (l). As a result, the above-mentioned differential voltage signal detected by the flaw detecting circuit 10 does not accurately correspond to the depth (d) of the inner surface flaw 14a, but originally contains an error signal. As described above with reference to FIG. 5, the value of the bias voltage signal of the DC voltage signal from the synchronous detector 9 varies in proportion to the distance (l). Therefore, the value of the DC voltage signal from the synchronous detector 9 and the value of the differential voltage signal from the flaw detection circuit 10 also vary in proportion to the distance (l). Therefore, if the changes in these signal values caused by the change in the distance (l) are not affected by the difference in the depth (d) of the inner surface flaw 14a, it would be possible to correct a detection error of the differential voltage signal resulting from the change in the distance (l) by amplifying the differential voltage signal from the flaw detecting circuit 10 at an amplification degree inversely proportional to the value of the bias voltage signal from the moving average circuit 11.

Figure 7:
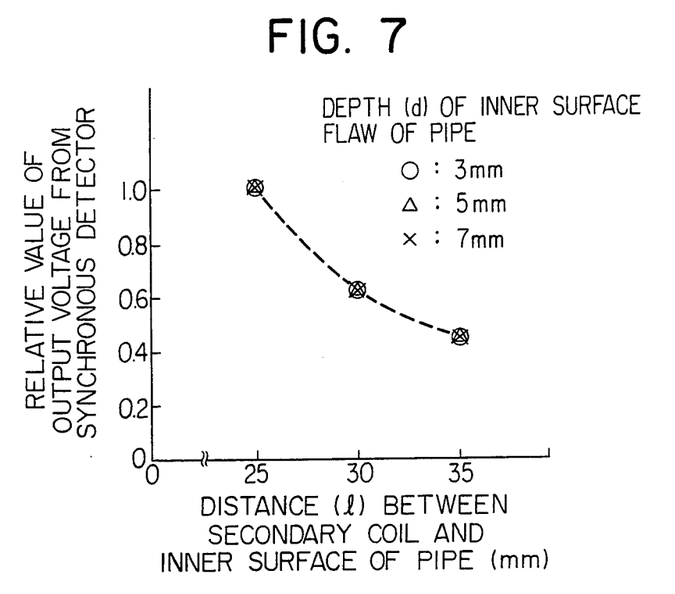
FIG. 7 is a graph illustrating the relationship between the relative value of the output voltage from the synchronous detector of the signal processing circuit, which is one of the components of the apparatus of the present invention shown in FIG. 1, on the one hand, and the distance (l) between the secondary coil and the inner surface of a pipe to be inspected, on the other hand.

FIG. 7 is a graph illustrating the relationship between the relative value of the output voltage from the synchronous detector of the signal processing circuit, on the one hand, and the distance (l) between the secondary coil and the inner surface of the pipe, on the other hand. In FIG. 7, the ordinate represents the relative value of the output voltage from the synchronous detector 9, corresponding to the value of the AC voltage signal from the secondary coil $S_1$ closest to the inner surface flaw 14a of the pipe 14, for example, of the plurality of secondary coils $S_1, \ldots, S_N$, in the case where the pair of primary coils $P_c$ reach the inner surface flaw 14a. The abscissa represents the distance (l) between that secondary coil $S_1$ and the inner surface of the pipe 14. The above-mentioned relative value of the output voltage from the synchronous detector 9 represented on the ordinate was obtained by dividing the value of the DC voltage signal from the synchronous detector 9 by the value of the DC voltage signal from the synchronous detector 9 for distance (l) of 25 mm between the secondary coil $S_1$ and the inner surface of the pipe 14. The inner surface flaw 14a was artificially made by a drill.

As is clear from FIG. 7, as the distance (l) between the secondary. coil $S_1$ and the inner surface of the pipe 14 varies from 25 mm to 30 mm, and from 30 mm to 35 mm, the relative value of the output voltage from the synchronous detector 9 decreases for all the depths (d) of the inner surface flaw 14a of 3 mm, 5 mm and 7 mm, whereas the extent of this decrease is the same for the same distance (l), and the ratio of the decrease in the above-mentioned relative value to the distance (l) remains the same without difference dependent on the depth (d) of the inner surface flaw 14a. More particularly, while the value of the DC voltage signal itself from the synchronous detector 9 contains a difference dependent on the depth (d) of the inner surface flaw 14a, the change in the output voltage from the synchronous detector 9 caused by the change in the distance (l) remains the same irrespective of the depth (d) of the inner surface flaw 14a. As described above, therefore, it is possible to correct a detection error of the differential voltage signal resulting from the change in the distance (l) by amplifying the differential voltage signal from the flaw detecting circuit 10 at an amplification degree inversely proportional to the value of the bias voltage signal from the moving average circuit 11.

More specifically, the detection error correcting circuit 13 amplifies the differential voltage signal from the flaw detecting circuit 10 for each of the plurality of secondary coils $S_1, \ldots, S_N$ at an amplification degree inversely proportional to the value of the bias voltage signal from the moving average circuit 11 for each of the plurality of secondary coils $S_1, \ldots, S_N$, thereby correcting a detection error of the differential voltage signal caused by a fluctuation in the distance (l) between each of the plurality of secondary coils $S_1, \ldots, S_N$ and the inner surface of the pipe 14.

Figure 8:
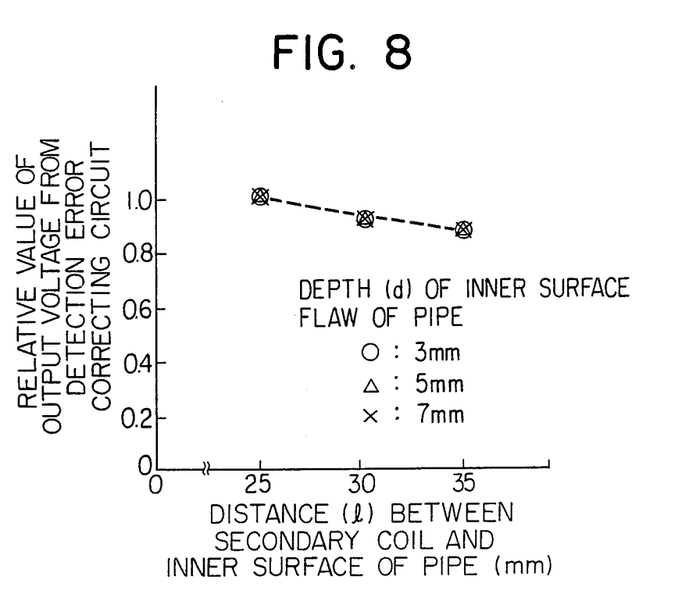
FIG. 8 is a graph illustrating the relationship between the relative value of the output voltage from the detection error correcting circuit of the signal processing circuit, which is one of the components of the apparatus of the present invention shown in FIG. 1, on the one hand, and the distance (l) between the secondary coil and the inner surface of a pipe to be inspected, on the other hand.

FIG. 8 is a graph illustrating the relationship between the relative value of the output voltage from the detection error correcting circuit of the signal processing circuit, on the one hand, and the distance (l) between the secondary coil and the inner surface of the pipe, on the other hand. In FIG. 8, the ordinate represents the relative value of the output voltage from the detection error correcting circuit 13 corresponding to the value of the differential voltage signal of the secondary coil $S_1$ closest to the inner surface flaw 14a of the pipe 14, for example, of the plurality of secondary coils $S_1, \ldots, S_N$, in the case where the pair of primary coils $P_c$ reach the inner surface flaw 14a. The abscissa represents the distance (l) between that secondary coil $S_1$ and the inner surface of the pipe 14. The above-mentioned relative value of the output voltage from the detection error correcting circuit 13 represented on the ordinate was obtained by dividing the value of the DC voltage signal from the detection error correcting circuit 13 by the value of the DC voltage signal from the detection error correcting circuit 13 for a distance (l) of 25 mm between the secondary coil $S_1$ and the inner surface of the pipe. The inner surface flaw 14a was artificially made by a drill.

As is clear from FIG. 8, the relative value of the output voltage from the detection error correcting circuit 13 shows the same value if the distance (l) between the secondary coil $S_1$ and the inner surface of the pipe 14 remains the same, irrespective of the depth (d) of the inner surface flaw 14a, and the ratio of the decrease in the above-mentioned relative value to the distance (l) is very small. More specifically, the DC voltage signal from the detection error correcting circuit 13 shows a value corresponding to the depth (d) of the inner surface flaw 14a even when the distance (l) varies, and in the DC voltage signal from the detection error correcting circuit 13, the detection error of the differential voltage signal from the flaw detecting circuit 10 caused by the change in the distance (l) has been corrected. Therefore, it is possible to accurately detect the depth (d) of the inner surface flaw 14a by using the above-mentioned DC voltage signal from the detection error correcting circuit 13.

According to the apparatus of the present invention, as described above in detail, in which the plurality of secondary coils forming part of the detecting probe are arranged at prescribed intervals in the circumferential direction of a pipe to be inspected in the space between the outer peripheral surface of the at least one primary coil forming part of the detecting probe and the inner peripheral surface of the pipe so that the axis of each of the plurality of secondary coils is parallel to the axis of the at least one primary coil, it is possible to accurately detect the presence and the depth of each of three or more inner surface flaws of each of a plurality of pipes forming a pipeline even when these inner surface flaws are present at close intervals in the axial direction of the pipe, thus providing industrially useful effects.

What is claimed is:

1. In apparatus for detecting a surface flaw of a pipeline using electromagnetic induction, which comprises:
   a pig capable of travelling along a plurality of pipes forming a pipeline;
   at least one primary coil mounted on said pig, said primary coil being arranged to interact electromagnetically with said pipeline, and a peripheral surface of said primary coil is spaced apart from a confronting peripheral surface of said pipeline by a prescribed distance to form a clearance space;
   a high frequency electric current generator for supplying high frequency electric current to said primary coil to produce an AC magnetic field, wherein a magnetic flux density of said AC magnetic field varies in response to a surface flaw of said pipeline;
   a plurality of secondary coils arranged at prescribed intervals in the circumferential direction of said pipeline in said clearance space, so that each of said plurality of secondary coils produces an AC voltage signal proportional to a flux density of an interlinking magnetic flux component, said interlinking component being of said AC magnetic field produced by said primary coil;
   a multiplexer mounted on said pig, said plurality of secondary coils being coupled to said multiplexer, and said multiplexer responding to AC voltage signals from said plurality of secondary coils sequentially in order of arrangement of said secondary coils; and
   a signal processing circuit comprising a synchronous detector, moving average circuit means and flaw detecting circuit means; said synchronous detector detecting said AC voltage signals from said plurality of secondary coils and converting said AC voltage signals into DC voltage signals; said moving average circuit means processing said DC voltage signals in a prescribed manner for each of said secondary coils to obtain processed DC voltage signals for each of said secondary coils; and said flaw detecting circuit means sequentially producing a voltage signal proportional to the depth of a detected surface flaw of said pipeline as a function of said DC voltage signals;
   the improvement comprising:
   said signal processing circuit includes a detection error correcting circuit for amplifying said voltage signal from said flaw detecting circuit means for each of said secondary coils, wherein said detection error correcting circuit includes means for setting an amplification factor of said detection error correcting circuit at a value inversely proportional to a value of said processed DC voltage signals from said moving average circuit means for each of said secondary coils, wherein an error in the voltage signal produced by said flaw detecting circuit means, caused by a fluctuation in distance between each of surface of said pipeline, is corrected.

2. The apparatus of claim 1, wherein said moving average circuit means includes means for sequentially obtaining bias voltage signals from the DC voltage signals for each of said secondary coils.

3. The apparatus of claim 2, wherein said flaw detecting circuit means includes means for substracting a bias voltage signal obtained by said moving average circuit means for each of said secondary coils, from a DC voltage signal generated by said synchronous detector which DC signal immediately follows an operation of said moving average circuit means for each secondary coil.

4. The apparatus according to claim 1, wherein said at least one primary coil is cylindrical and arranged coaxially within said pipeline, the outer peripheral surface of said primary coil confronts the inner peripheral surface of said pipeline, and said plurality of secondary coils are cylindrical and arranged in the clearance space between the outer peripheral surface of said primary coil and the inner peripheral surface of said pipeline with the axes of the secondary coils parallel to the axis of said primary coil, so that the interlinking magnetic flux component of the AC magnetic field is parallel to the axial direction of each of said secondary coils and the apparatus is capable of detecting an inner surface flaw of said pipeline.

5. The apparatus according to claim 1, wherein said synchronous detector includes means responsive to the high frequency electric current from said current generator for enabling sequential and synchronous detection of the AC voltage signals from said secondary coils.

* * * * *